(12) United States Patent
Nakamura et al.

(10) Patent No.: US 11,009,610 B2
(45) Date of Patent: May 18, 2021

(54) RADIATION DETECTION SYSTEM, RADIATION OUTPUT DEVICE, AND RADIATION DETECTION DEVICE

(71) Applicant: FUJIFILM Corporation, Tokyo (JP)

(72) Inventors: Kenji Nakamura, Kanagawa (JP); Kouichi Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/550,300

(22) Filed: Aug. 26, 2019

(65) Prior Publication Data

US 2020/0025947 A1  Jan. 23, 2020

Related U.S. Application Data

(63) Continuation of application No. PCT/JP2018/006572, filed on Feb. 22, 2018.

(30) Foreign Application Priority Data

Feb. 28, 2017 (JP) .............................. JP2017-036362

(51) Int. Cl.
*G01T 1/16* (2006.01)
*G01N 23/04* (2018.01)
*G01T 1/15* (2006.01)

(52) U.S. Cl.
CPC .............. *G01T 1/16* (2013.01); *G01N 23/04* (2013.01); *G01T 1/15* (2013.01)

(58) Field of Classification Search
CPC .............. G01N 23/04; G01T 1/15; G01T 1/16
See application file for complete search history.

(56) References Cited

U.S. PATENT DOCUMENTS 9,445,030 B2  9/2016  Yagi et al.
2009/0109313 A1  4/2009  Liu et al.
(Continued)

FOREIGN PATENT DOCUMENTS

JP  2012161552  8/2012
JP  2012250023  12/2012
(Continued)

OTHER PUBLICATIONS

"Office Action of Japan Counterpart Application," with English translation thereof, dated Nov. 5, 2019, p. 1-p. 5.
(Continued)

*Primary Examiner* — David P Porta
*Assistant Examiner* — Fani Boosalis
(74) *Attorney, Agent, or Firm* — JCIPRNET

(57) ABSTRACT

The present disclosure provides a radiation detection system, a radiation output device, and a radiation detection device. The radiation detection system includes a radiation output device having a radiation generation unit and an output control unit that controls output of radiation, and a radiation detection device having a radiographic image detector that detects radiation output from the radiation output device, and a recognition unit that recognizes whether radiation has been output from the radiation output device on the basis of a radiation detection signal output from the radiographic image detector. The output control unit causes radiation with a preset waveform pattern to be output from a time point of the start of outputting of the radiation, and the recognition unit recognizes the waveform pattern, thereby recognizing the start of outputting of the radiation.

16 Claims, 4 Drawing Sheets

(56) References Cited

U.S. PATENT DOCUMENTS

| | | | |
|---|---|---|---|
| 2010/0054406 A1* | 3/2010 | Kitano | G01N 23/04 378/62 |
| 2012/0201357 A1 | 8/2012 | Watanabe et al. | |
| 2012/0288061 A1 | 11/2012 | Okada | |
| 2015/0043715 A1 | 2/2015 | Kuwabara et al. | |
| 2015/0223312 A1 | 8/2015 | Kikuchi et al. | |
| 2015/0351715 A1 | 12/2015 | Ota et al. | |

FOREIGN PATENT DOCUMENTS

| | | |
|---|---|---|
| JP | 2013094454 | 5/2013 |
| JP | 5270790 | 8/2013 |
| JP | 2015146877 | 8/2015 |
| JP | 2015230197 | 12/2015 |
| JP | 2016025465 | 2/2016 |

OTHER PUBLICATIONS

"International Search Report (Form PCT/ISA/210) of PCT/JP2018/006572," dated May 29, 2018, with English translation thereof, pp. 1-5.

"Written Opinion of the International Searching Authority (Form PCT/ISA/237) of PCT/JP2018/006572," dated May 29, 2018, with English translation thereof, pp. 1-10.

* cited by examiner

FIG. 5
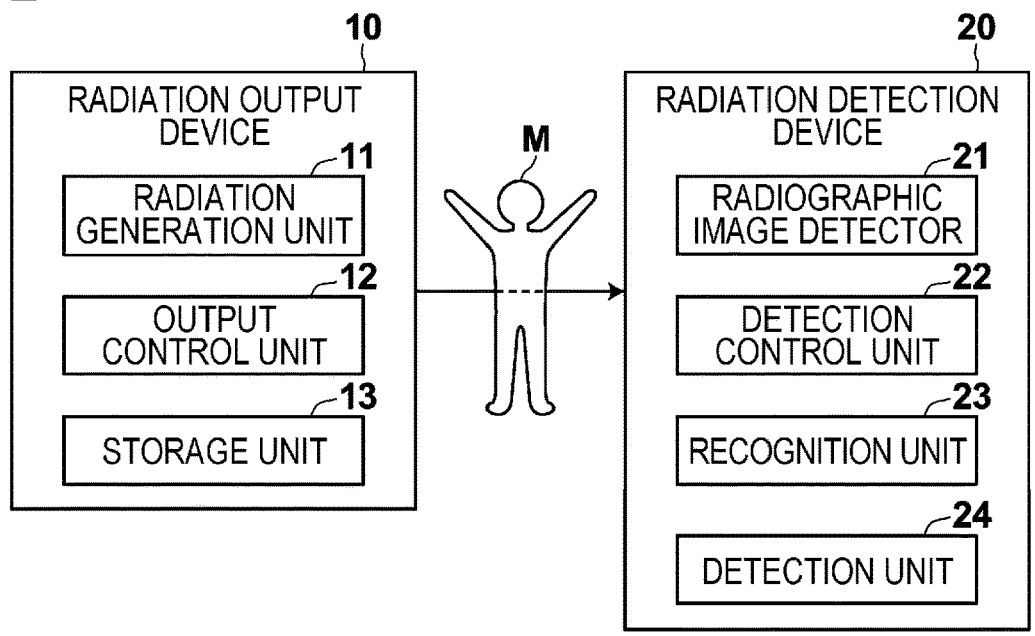
FIG. 6
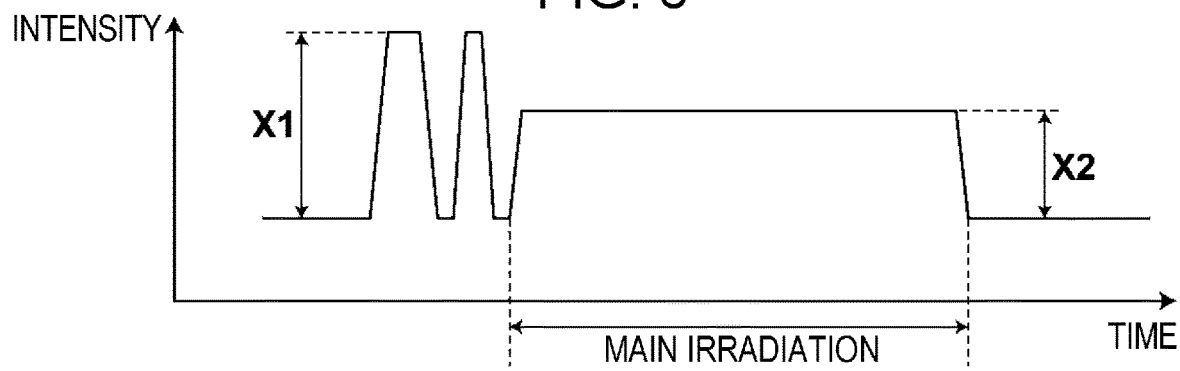
FIG. 7
| IMAGING SITE | FIRST INTENSITY |
|---|---|
| CHEST | X1_1 |
| ABDOMEN | X1_2 |
| LEG | X1_3 |
| HAND | X1_4 |
| ⋮ | ⋮ |

FIG. 8

| PATIENT INFORMATION | FIRST INTENSITY |
|---|---|
| PATIENT 1 | X1_5 |
| PATIENT 2 | X1_6 |
| PATIENT 3 | X1_7 |
| PATIENT 4 | X1_8 |
| ⋮ | ⋮ |

# RADIATION DETECTION SYSTEM, RADIATION OUTPUT DEVICE, AND RADIATION DETECTION DEVICE

CROSS-REFERENCE TO RELATED APPLICATION

The present application is a Continuation of PCT International Application No. PCT/JP2018/006572 filed on Feb. 22, 2018, which claims priority under 35 U.S.C. § 119(a) to Japanese Patent Application No. 2017-036362 filed on Feb. 28, 2017. Each of the above applications is hereby expressly incorporated by reference, in its entirety, into the present application.

BACKGROUND

Technical Field

The present disclosure relates to a radiation detection system that outputs radiation to a photographic subject and detects radiation transmitted through the photographic subject, and a radiation output device and a radiation detection device in the radiation detection system.

Description of the Related Art

A radiation detection system constituted by a radiation output device including an X-ray tube and so on, and a radiation detection device including a radiographic image detector such as an FPD (Flat Panel Detector) that detects radiation output from the radiation output device and transmitted through a patient has been proposed in the related art (see, for example, JP2016-25465A).

In the radiation detection system, when no radiation is emitted, the radiographic image detector undergoes preparation operation control so as to periodically reset an electric charge signal accumulated by leakage current. When the emission of radiation is started, a transition occurs from the preparation operation control to electric charge accumulation control. In the electric charge accumulation control, an electric charge signal corresponding to a dose of radiation transmitted through the patient is accumulated in each pixel of the radiographic image detector.

To allow the radiographic image detector to transition from the preparation operation control to the electric charge accumulation control in response to the start of emission of radiation, it is necessary to provide synchronization between the radiation output device and the radiation detection device.

Examples of the method for providing synchronization between the radiation output device and the radiation detection device include a method for exchanging a signal for permitting the start of outputting of radiation or a signal indicating that radiation is being output between the radiation output device and the radiation detection device by using wired or wireless connection.

Other examples include a method for recognizing the start of outputting of radiation on the basis of a signal detected by the radiographic image detector.

SUMMARY

The latter method among the methods for providing synchronization described above has a problem in that if radiation output from the radiation output device has a low intensity, the radiation is difficult to discriminate from noise when detected by the radiographic image detector, and the start of outputting of the radiation is not recognizable or it takes time until the start of outputting of the radiation is recognized.

In particular, a portable radiation output device and radiation detection device used in a patient's room in the hospital, the patient's home, and the like have been proposed in recent years. To suppress the amount of radiation exposure in the surroundings, it is preferable that the dose of radiation output from the radiation output device be low, and the problem described above is likely to occur in the portable radiation output device described above.

To address the problem described above, it is an object of the present disclosure to provide a radiation detection system in which a radiation detection device is capable of accurately detecting the start of outputting of radiation from a radiation output device, the radiation output device, and the radiation detection device.

A radiation detection system according to an aspect of the present disclosure includes a radiation output device having a radiation generation unit that generates radiation, and an output control unit that controls output of the radiation, and a radiation detection device having a detection unit that detects the radiation output from the radiation output device and outputs a radiation detection signal, and a recognition unit that recognizes whether radiation has been output from the radiation output device on the basis of the radiation detection signal output from the detection unit. The output control unit of the radiation output device causes radiation with a preset waveform pattern to be output from a time point of a start of outputting of the radiation. The recognition unit of the radiation detection device recognizes the waveform pattern, thereby recognizing that radiation has been output from the radiation output device.

In the radiation detection system according to an aspect of the present disclosure, furthermore, the output control unit can cause radiation with the waveform pattern having a plurality of pulses to be output.

In the radiation detection system according to an aspect of the present disclosure, furthermore, the output control unit can control a width and interval of the pulses.

In the radiation detection system according to an aspect of the present disclosure, furthermore, the output control unit can cause the radiation with the waveform pattern to be output at a first intensity and then cause the radiation to be output at a second intensity, and the first intensity can be higher than the second intensity.

In the radiation detection system according to an aspect of the present disclosure, furthermore, the output control unit can change the first intensity for each imaging site or patient to be irradiated with the radiation output from the radiation output device.

In the radiation detection system according to an aspect of the present disclosure, furthermore, the radiation detection device can include a radiographic image detector that detects radiation output from the radiation output device and transmitted through a photographic subject, and the radiographic image detector can start accumulation of a detection signal of the radiation transmitted through the photographic subject on the basis of a time point when an output of radiation is recognized by the recognition unit.

In the radiation detection system according to an aspect of the present disclosure, furthermore, the detection unit of the radiation detection device can be at least a portion of the radiographic image detector.

A radiation output device according to an aspect of the present disclosure is a radiation output device including a radiation generation unit that generates radiation, and an output control unit that controls output of the radiation. The output control unit stores in advance a waveform pattern of radiation for allowing a radiation detection device that detects the radiation to recognize a start of outputting of the radiation, and causes radiation with the waveform pattern to be output from a time point of a start of outputting of the radiation.

In the radiation output device according to an aspect of the present disclosure, furthermore, the output control unit can cause radiation with the waveform pattern having a plurality of pulses to be output.

In the radiation output device according to an aspect of the present disclosure, furthermore, the output control unit can control a width and interval of the pulses.

In the radiation output device according to an aspect of the present disclosure, furthermore, the output control unit can cause the radiation with the waveform pattern to be output at a first intensity and then cause the radiation to be output at a second intensity, and the first intensity can be higher than the second intensity.

In the radiation output device according to an aspect of the present disclosure, furthermore, the output control unit can change the first intensity for each imaging site or patient to be irradiated with the radiation output from the radiation output device.

A radiation detection device according to an aspect of the present disclosure includes a radiographic image detector that detects radiation output from a radiation output device and transmitted through a photographic subject, a detection control unit that controls the radiographic image detector, and a recognition unit that recognizes whether radiation has been output from the radiation output device. The recognition unit recognizes that radiation with a preset waveform pattern has been detected, thereby recognizing that radiation has been output from the radiation output device. The detection control unit controls the radiographic image detector on the basis of a time point when an output of radiation is recognized by the recognition unit to start accumulation of an electric charge signal generated by irradiation with the radiation transmitted through the photographic subject.

In the radiation detection device according to an aspect of the present disclosure, furthermore, the recognition unit can recognize the waveform pattern having a plurality of pulses.

In the radiation detection device according to an aspect of the present disclosure, furthermore, the recognition unit can recognize a width and interval of the pulses.

In the radiation detection device according to an aspect of the present disclosure, furthermore, the recognition unit can recognize the waveform pattern on the basis of a radiation detection signal output from the radiographic image detector.

According to a radiation detection system, a radiation output device, and a radiation detection device according to an aspect of the present disclosure, the radiation output device outputs radiation with a preset waveform pattern from the time point of the start of outputting of the radiation, and the radiation detection device recognizes the waveform pattern, thereby recognizing that radiation has been output from the radiation output device. This enables the radiation detection device to easily discriminate a radiation detection signal obtained by detecting the radiation output from the radiation output device from noise and to accurately detect the start of outputting of radiation from the radiation output device.

BRIEF DESCRIPTION OF THE DRAWINGS

Exemplary embodiments of the present invention will be described in detail based on the following figures, wherein:

FIG. 5 is a block diagram illustrating a schematic configuration of another embodiment of the radiation detection system according to an aspect of the present disclosure;

FIG. 6 is a diagram illustrating another example waveform pattern of radiation output from an embodiment of the radiation output device according to an aspect of the present disclosure;

FIG. 7 is a diagram illustrating a table in which imaging sites and first intensities at the start of outputting of radiation are associated with each other; and FIG. 8 is a diagram illustrating a table in which patient information and first intensities at the start of outputting of radiation are associated with each other.

DETAILED DESCRIPTION

Figure 1:
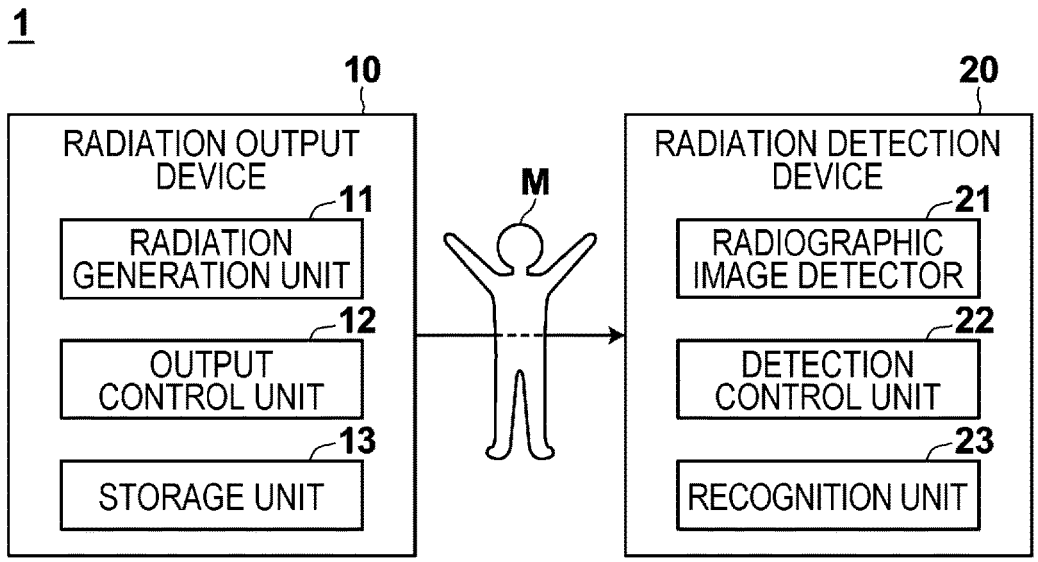
FIG. 1 is a block diagram illustrating a schematic configuration of a radiation detection system according to an embodiment of the present disclosure.

The following describes a radiation detection system, a radiation output device, and a radiation detection device according to an embodiment of the present disclosure in detail with reference to the drawings. FIG. 1 is a block diagram illustrating a schematic configuration of the radiation detection system of this embodiment.

As illustrated in FIG. 1, a radiation detection system 1 of this embodiment includes a radiation output device 10 and a radiation detection device 20. The radiation output device 10 is preferably portable, and the radiation detection device 20 is also preferably a portable cassette. However, the present disclosure is not limited to a portable radiation detection system, and is also applicable to mountable radiation detection systems such as a radiation detection system that captures an image of a photographic subject in standing position and a radiation detection system that captures an image of a photographic subject in lying position.

The radiation output device 10 outputs radiation to a photographic subject M such as a patient. The radiation output device 10 includes a radiation generation unit 11 that generates radiation, an output control unit 12 that controls output of the radiation, and a storage unit 13.

The radiation generation unit 11 includes a radiation source such as an X-ray tube. The radiation generation unit 11 generates radiation due to the application of a high voltage.

The output control unit 12 includes, for example, a CPU (Central Processing Unit) and so on. The output control unit 12 controls output of radiation from the radiation output device 10. Specifically, the output control unit 12 controls a tube voltage and tube current to be applied to the radiation generation unit 11, such that the output control unit 12 controls the tube voltage or tube current to control the intensity of radiation to be emitted from the radiation generation unit 11 and the duration of emission.

To allow the radiation detection device 20 to recognize that the radiation output device 10 has started outputting radiation, the output control unit 12 controls the radiation generation unit 11 to output radiation with a preset waveform pattern from the time point of the start of outputting of the radiation.

Figure 2:
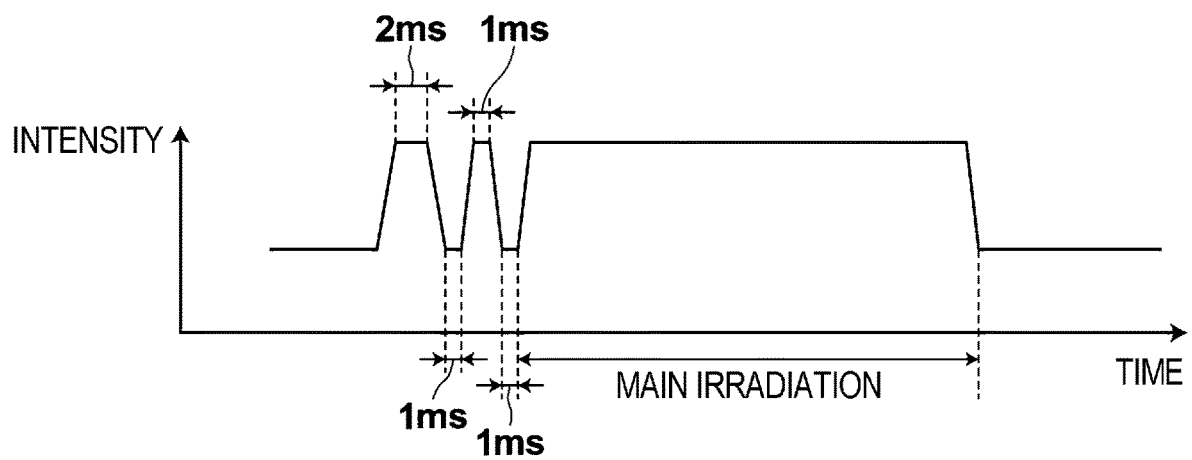
FIG. 2 is a diagram illustrating an example waveform pattern of radiation output from a radiation output device according to an embodiment of the present disclosure.

For example, the output control unit 12 of this embodiment causes a waveform pattern having two pulses, as illustrated in FIG. 2, to be output. More specifically, the output control unit 12 outputs, as a waveform pattern, radiation with a pulse width of 2 ms and then radiation with a pulse width of 1 ms after an interval of 1 ms, which is followed by an interval of 1 ms. After the interval of 1 ms, the output control unit 12 causes radiation to be output for main irradiation to capture a radiographic image of the subject. The waveform pattern is not limited to that in the example illustrated in FIG. 2, and three or more pulses may be used.

When a plurality of pulses are to be output as a waveform pattern, as in this embodiment, it is preferable to output pulses having different pulse widths. This can improve the accuracy of a recognition unit described below to recognize a waveform pattern.

The waveform pattern may be made changeable by the output control unit 12 accepting a change of the waveform pattern. For example, the waveform pattern may be changed for each hospital, clinical department, or technician.

In this embodiment, the tube voltage or tube current of the radiation generation unit 11 is controlled to output radiation with the waveform pattern described above. However, this is not limiting, and, for example, a diaphragm, a shutter, or the like may be disposed and controlled to control the output of radiation with the waveform pattern described above.

The storage unit 13 stores information on the waveform pattern described above. The storage unit 13 is constituted by a semiconductor memory, a register, or the like, and stores information on the pulse width and interval of the waveform pattern. The output control unit 12 controls the radiation generation unit 11 on the basis of the information stored in the storage unit 13 to output radiation with a preset waveform pattern.

The radiation detection device 20 includes a radiographic image detector 21, a detection control unit 22, and a recognition unit 23.

The radiographic image detector 21 detects radiation output from the radiation output device 10 and transmitted through the photographic subject M and outputs a radiation detection signal. Examples of the radiographic image detector 21 include a device including a scintillator (fluorescent body) that converts incident radiation into visible light and a TFT (Thin Film Transistor) active matrix substrate. The radiographic image detector 21 is not limited to this, and may be a so-called direct-conversion radiographic image detector that converts incident radiation directly into an electric charge signal. In this embodiment, the radiographic image detector 21 corresponds to a detection unit according to an aspect of the present disclosure.

Figure 3:
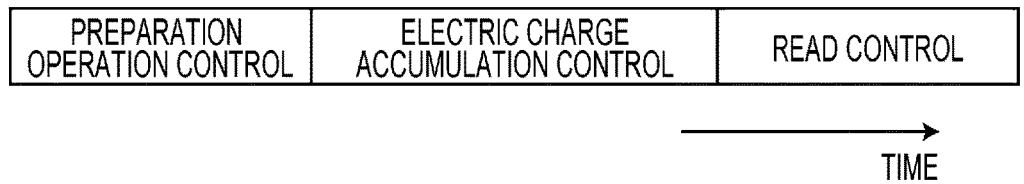
FIG. 3 is a diagram for describing operation control for a radiographic image detector.

The detection control unit 22 includes, for example, a CPU and so on. The detection control unit 22 controls the operation of the radiographic image detector 21. The operation control for the radiographic image detector 21 includes preparation operation control, electric charge accumulation control, and read control, as illustrated in FIG. 3.

During the period of the preparation operation control for the radiographic image detector 21, a high voltage is applied to the radiographic image detector 21 to allow the radiographic image detector 21 to detect radiation. During the period of the preparation operation control, a radiation detection signal is read from the radiographic image detector 21 in a preset detection period, and is output to the recognition unit 23. The detection period described above is set to a longer period than the period of the waveform pattern described above.

As the radiation detection signal output from the radiographic image detector 21 to the recognition unit 23 during the period of the preparation operation control, a signal output from one preset pixel (detection element) in the radiographic image detector 21 may be used, or the sum, mean, median, or the like of signals output from some pixels or the sum, mean, median, or the like of signals output from all the pixels may be used.

The recognition unit 23 determines, based on the radiation detection signal input during the period of the preparation operation control, whether the radiation detection signal corresponds to the waveform pattern described above. The recognition unit 23 recognizes that the radiation detection signal corresponds to the waveform pattern, thereby recognizing that radiation has been output from the radiation output device 10.

When the recognition unit 23 recognizes that radiation has been output from the radiation output device 10, a recognition signal is output from the recognition unit 23 to the detection control unit 22. The detection control unit 22 starts the electric charge accumulation control at the time point when the recognition signal is input. Specifically, the detection control unit 22 controls the radiographic image detector 21 to start accumulation of electric charge generated by irradiation with radiation transmitted through the photographic subject M. The accumulation of electric charge is performed for a preset main irradiation period.

Then, the detection control unit 22 starts the read control from the time when the main irradiation period ends. Specifically, the detection control unit 22 controls the radiographic image detector 21 to start reading an electric charge signal accumulated during the main irradiation period. A radiation detection signal corresponding to the electric charge signal read from the radiographic image detector 21 is stored in a storage medium such as a memory disposed in the radiation detection device 20. The radiation detection signal stored in the storage medium is subjected to predetermined signal processing and is then output to a device such as a console.

Figure 4:
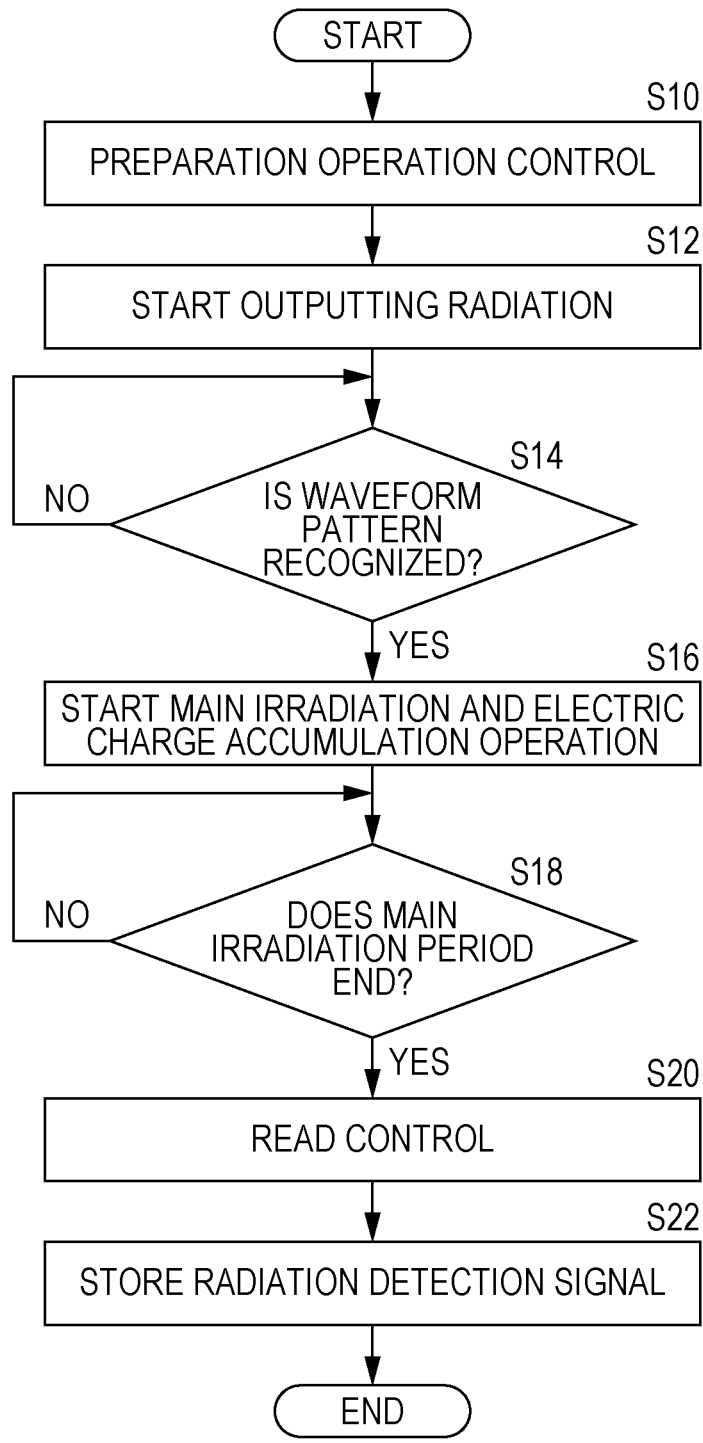
FIG. 4 is a flowchart for describing the operation of an embodiment of the radiation detection system according to an aspect of the present disclosure.

Next, the operation of the radiation detection system of this embodiment will be described with reference to a flowchart illustrated in FIG. 4.

First, in the radiation detection device 20, the detection control unit 22 performs control to start the preparation operation of the radiographic image detector 21 (S10).

After the photographic subject M is placed at a predetermined position of the radiographic image detector 21, a technician or the like inputs a radiation exposure instruction, and the radiation output device 10 starts outputting radiation in accordance with the radiation exposure instruction (S12).

The radiation output device 10 outputs radiation with the waveform pattern described above from the time point of the start of outputting of the radiation, and the radiation with the waveform pattern is detected by the radiographic image detector 21 of the radiation detection device 20. A radiation detection signal output from the radiographic image detector 21 is input to the recognition unit 23, and the recognition unit 23 recognizes whether a radiation detection signal corresponding to the radiation with the waveform pattern described above has been input. If it is recognized that a radiation detection signal corresponding to the radiation with the waveform pattern described above has been input (S14, YES), the recognition unit 23 outputs a recognition signal to the detection control unit 22.

The radiation output device 10 starts main irradiation after outputting the radiation with the waveform pattern described above. On the other hand, the detection control unit 22 of the radiation detection device 20 controls the radiographic image detector 21 to start an electric charge accumulation operation from the time point when the recognition signal is input (S16).

Then, at the time point when the radiation is output for the preset main irradiation period (S18, YES), the radiation output device 10 stops outputting the radiation. On the other hand, the detection control unit 22 of the radiation detection device 20 starts the reading operation of the radiographic image detector 21 (S20).

Then, the radiation detection signal output from the radiographic image detector 21 is stored in the storage medium such as a memory (S22).

According to the radiation detection system 1 of the embodiment described above, the radiation output device 10 outputs radiation with a preset waveform pattern from the time point of the start of outputting of the radiation, and the radiation detection device 20 recognizes the waveform pattern, thereby recognizing that radiation has been output from the radiation output device 10. Thus, a radiation detection signal obtained by detecting the radiation output from the radiation output device 10 can be easily discriminated from noise, and the start of outputting of radiation from the radiation output device 10 can be accurately detected.

In the radiation detection system 1 of the embodiment described above, the recognition unit 23 recognizes output of radiation by using a radiation detection signal output from the radiographic image detector 21. However, this is not limiting, and, as illustrated in FIG. 5, a detection unit 24 that detects radiation output from the radiation output device 10 may be disposed separately from the radiographic image detector 21. The recognition unit 23 may recognize output of radiation by using a radiation detection signal output from the detection unit 24.

In addition, as in the embodiment described above, when radiation with a preset waveform pattern is to be output from the radiation output device 10, as illustrated in FIG. 6, preferably, the radiation with the waveform pattern is output at a first intensity X1, and then radiation with a second intensity X2 is output, where the first intensity X1 is higher than the second intensity X2. In this way, setting the first intensity X1 higher than the second intensity X2 can improve the accuracy of the recognition unit 23 to recognize a waveform pattern.

As described above, furthermore, when radiation with a waveform pattern is to be output at the first intensity X1, the first intensity X1 may be changed for each imaging site or patient that is irradiated with the radiation. Specifically, as illustrated in FIG. 7, a table in which imaging sites and first intensities are associated with each other may be disposed, or, as illustrated in FIG. 8, a table in which patient information and first intensities are associated with each other may be disposed. These tables may be referenced to change the first intensity X1 of the radiation with the waveform pattern. In this way, changing the first intensity X1 can prevent an unnecessary increase in the amount of radiation exposure to the patient.

The disclosure of JP2017-036362 is incorporated herein by reference in its entirety.

All the documents, patent applications, and technical standards mentioned in this specification are incorporated herein by reference to the same extent as if each individual document, patent application, and technical standard were specifically and individually indicated to be incorporated by reference.

What is claimed is:

1. A radiation detection system comprising:
    a radiation output device having a radiation generation unit that generates radiation, and a processor that controls output of the radiation; and
    a radiation detection device having a radiation detector that detects the radiation output from the radiation output device and outputs a radiation detection signal, and a recognition circuit that recognizes whether radiation has been output from the radiation output device on the basis of the radiation detection signal output from the radiation detector, wherein
    the processor of the radiation output device causes radiation with a preset waveform pattern to be output from a time point of a start of outputting of the radiation, and
    the recognition circuit of the radiation detection device recognizes the waveform pattern, thereby recognizing that radiation has been output from the radiation output device.

2. The radiation detection system according to claim 1, wherein
    the processor causes radiation with the waveform pattern having a plurality of pulses to be output.

3. The radiation detection system according to claim 2, wherein
    the processor controls a width and interval of the pulses.

4. The radiation detection system according to claim 1, wherein
    the processor causes the radiation with the waveform pattern to be output at a first intensity and then causes the radiation to be output at a second intensity, and
    the first intensity is higher than the second intensity.

5. The radiation detection system according to claim 4, wherein
    the processor changes the first intensity for each imaging site or patient to be irradiated with the radiation output from the radiation output device.

6. The radiation detection system according to claim 1, wherein
    the radiation detection device comprises a radiographic image detector that detects radiation output from the radiation output device and transmitted through a photographic subject, and
    the radiographic image detector starts accumulation of a detection signal of the radiation transmitted through the photographic subject on the basis of a time point when an output of radiation is recognized by the recognition circuit.

7. The radiation detection system according to claim 6, wherein
    the radiation detector of the radiation detection device is at least a portion of the radiographic image detector.

8. A radiation output device comprising a radiation generation unit that generates radiation, and a processor that controls output of the radiation, wherein
    the processor stores in advance a waveform pattern of radiation for allowing a radiation detection device that detects the radiation to recognize a start of outputting of the radiation, and causes radiation with the waveform pattern to be output from a time point of a start of outputting of the radiation.

9. The radiation output device according to claim 8, wherein the processor causes radiation with the waveform pattern having a plurality of pulses to be output.

10. The radiation output device according to claim 9, wherein
the processor controls a width and interval of the pulses.

11. The radiation output device according to claim 8, wherein
the processor causes the radiation with the waveform pattern to be output at a first intensity and then causes the radiation to be output at a second intensity, and
the first intensity is higher than the second intensity.

12. The radiation output device according to claim 11, wherein
the processor changes the first intensity for each imaging site or patient to be irradiated with the radiation output from the radiation output device.

13. A radiation detection device comprising:
a radiographic image detector that detects radiation output from a radiation output device and transmitted through a photographic subject;
a controller that controls the radiographic image detector; and
a recognition circuit that recognizes whether radiation has been output from the radiation output device, wherein
the recognition circuit recognizes that radiation with a preset waveform pattern has been detected from the radiographic image detector, thereby recognizing that radiation has been output from the radiation output device, and
the controller controls the radiographic image detector on the basis of a time point when an output of radiation is recognized by the recognition circuit to start accumulation of an electric charge signal generated by irradiation with the radiation transmitted through the photographic subject.

14. The radiation detection device according to claim 13, wherein
the recognition circuit recognizes the waveform pattern having a plurality of pulses.

15. The radiation detection device according to claim 14, wherein
the recognition circuit recognizes a width and interval of the pulses.

16. The radiation detection device according to claim 13, wherein
the recognition circuit recognizes the waveform pattern on the basis of a radiation detection signal output from the radiographic image detector.

* * * * *